United States Patent [19]

Kaneko et al.

[11] Patent Number: 5,118,405
[45] Date of Patent: Jun. 2, 1992

[54] LUMINESCENT PROBE COMPLEX FOR MEASURING PH AND METHOD FOR MEASURING PH

[75] Inventors: Masao Kaneko, Tokyo; Tetsuo Asakura, Koganei; Hideki Nakamura, Fuji; Takeshi Shimomura, Fuji; Hiroshi Sugise, Fuji, all of Japan

[73] Assignees: Terumo Kabushiki Kaisha, Tokyo; Rikagaku Kenkyusho, Wako, both of Japan

[21] Appl. No.: 582,176

[22] PCT Filed: Mar. 24, 1989

[86] PCT No.: PCT/JP89/00314
  § 371 Date: Sep. 25, 1990
  § 102(e) Date: Sep. 25, 1990

[87] PCT Pub. No.: WO89/09400
  PCT Pub. Date: Oct. 5, 1989

[30] Foreign Application Priority Data

Mar. 25, 1988 [JP] Japan .................. 63-71630

[51] Int. Cl.⁵ .............................. G01N 27/26
[52] U.S. Cl. ........................ 204/433; 204/416; 204/418
[58] Field of Search ............. 502/185, 166, 158, 167; 204/416, 433, 153.21, 431, 403; 252/431, 301.33; 436/542

[56] References Cited

U.S. PATENT DOCUMENTS

| | | | |
|---|---|---|---|
| 4,179,403 | 12/1979 | Kim et al. | 252/431 |
| 4,293,310 | 10/1981 | Weber | 436/542 |
| 4,582,589 | 4/1986 | Ushizawa et al. | 204/433 |
| 4,708,494 | 11/1987 | Kleinerman | 252/301.33 |
| 4,874,736 | 10/1989 | Drent | 502/167 |
| 4,892,640 | 1/1990 | Wolfbeis et al. | 204/416 |

FOREIGN PATENT DOCUMENTS 244929 11/1987 European Pat. Off. .

OTHER PUBLICATIONS

Analytical Chemistry, vol. 54, No. 4, Apr., 1982, "pH Sensor Based on Immobilized Fluoresceinamine" by Linda A. Saari, et al., pp. 821-823.

Primary Examiner—John Niebling
Assistant Examiner—Bruce Bell
Attorney, Agent, or Firm—Oblon, Spivak, McClelland, Maier & Neustadt

[57] ABSTRACT

A luminescent probe complex for measuring pH comprising, polypyridine ligands having ion dissociable substituents on their carbon rings and a transition metal ion selected from the elements of the VIII group of the periodic table.

Also disclosed is a luminescent probe membrane for measuring pH wherein the probe complex is contained in a macromolecular membrane. Further disclosed is a device for measuring pH wherein the probe membrane is immobilized at the tip of an optical fiber.

A method for measuring pH using the above are also disclosed. The present invention enables measurement of pH of microenvironments.

2 Claims, 3 Drawing Sheets

FIG. 2(a)
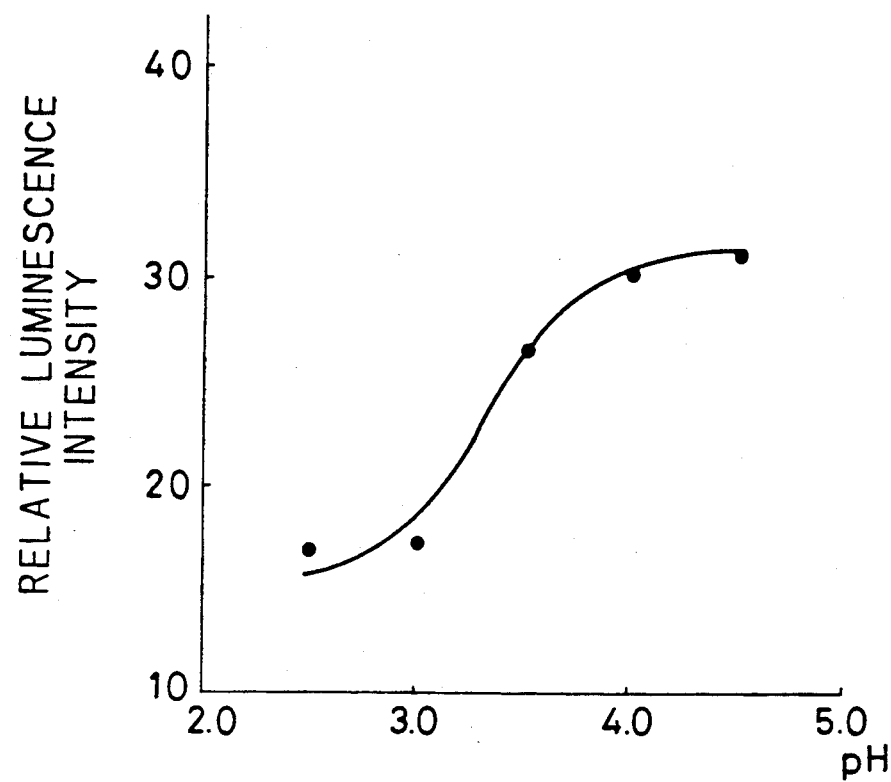
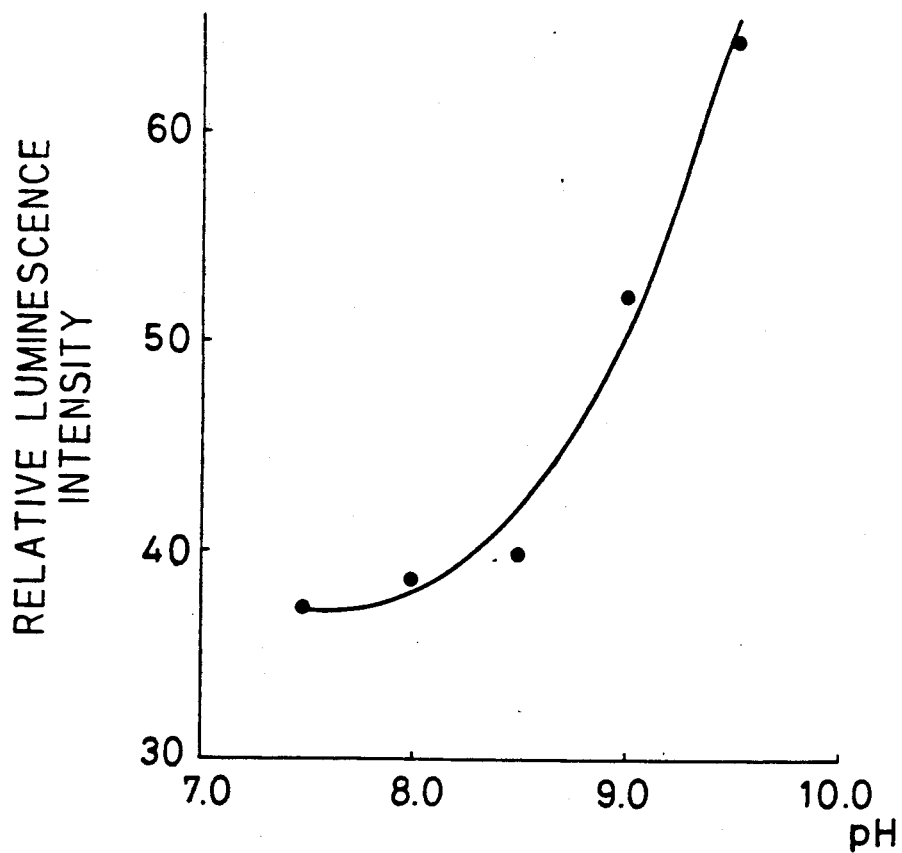
FIG. 2(b)

LUMINESCENT PROBE COMPLEX FOR MEASURING PH AND METHOD FOR MEASURING PH

TECHNICAL FIELD

The present invention relates to a method for pH measurement with a luminescent probe, a new luminescent probe complex for measuring pH, a luminescent probe membrane, a device for measuring pH and a method for measuring pH using the device.

BACKGROUND ART

Heretofore, devices have been known that use an electrode for measuring pH comprising a glass electrode and a reference electrode. Devices have also been known which use pigments for measuring pH. However, a pH measuring technique using a luminescent complex and a probe incorporating the complex have not been known in the art.

With the conventional pH measuring techniques, it is difficult to measure proton concentrations in a micro environment such as within a membrane. A technique of measuring pH locally, on a molecular scale has been long sought after in the art.

Therefore, it is an object of the present invention to provide a new luminescent probe complex for measuring pH which enables the measurement of pH easily in local areas, a luminescent probe membrane, a device for measuring pH and a method for measuring pH using the device.

DISCLOSURE OF INVENTION

The present invention relates to a luminescent probe complex for measuring pH comprising a polypyridine ligand having ion dissociable substituents in its carbon ring and transition metal ions selected from the elements of group VIII of the periodic table.

The present invention further relates to an luminescent probe membrane for measuring pH in which the above luminescent probe complex is contained in a macromolecular membrane.

The present invention further relates to a device for measuring pH in which the above luminescent probe membrane is immobilized at the tip of an optical fiber.

The present invention further relates to a method for measuring pH in which the luminescence intensity of the excited state of the above luminescent probe complex is measured.

The present invention will now be further explained in detail.

The luminescent probe complexes according to the present invention are complexes comprising polypyridine ligands having carboxyl, sulfate, hydroxy, ammonium or pyridinium groups etc. as ion-dissociable substituents on their respective carbon rings and a transition metal ion selected from the elements of group VIII of the periodic table.

The above polypyridine ligands include 4,4'-dicarboxy-2,2'-bipyridine-4,4'-disulfonic acid-2,2'-bipyridine, vasophenanthroline disulfonic acid, etc.

The transition metal ions include ions such as ruthenium, iridium, osmium, iron, rhodium ions.

The complexes used in the luminescent probe include tris (4,4'-dicarboxy-2,2'-bipyridine) ruthenium (II) complex (hereinafter referred to as "Ru(DCbpy)$_3^{2+}$, tris (4,4'-disulfonic acid-2,2'-bipyridine) ruthenium (II) complex, tris (vasophenanthroline disulfonic acid) ruthenium (II) complex, tris (4,4'-dicarboxy-2,2'-bipyridine) iridium (II) complex, tris (vasophenanthroline disulfonic acid) Fe (II) complex etc.

These luminescent probe complexes of the present invention luminesce from the excited state (mainly the triplet state) when the complexes, in solution or immobilized in a membrane, are irradiated with light having the maximum absorbance wavelength ($\lambda$ max) or a wavelength near $\lambda$ max. The present inventors have discovered that the luminescence intensity of the complexes of the present invention depends on the proton concentration in a system in which they are contained. This pH dependency of the luminescence intensity is based on the fact that dissocation of a substituent on the ligand depends on the proton concentration. The dissociation of the substituents depending on the proton concentration changes the charge state of the complex, which brings about a change in the luminescence intensity. The luminescence intensity of the complex is therefore dependent on the pH.

The luminescent probe complex does not influence the pH of the solution to be examined when dispersed in the solution. The complex is therefore suitable for being used to measure pH in solution. The complex can also be used by dispersing it in a macromolecular membrane.

When the complex is used in the form of a macromolecular membrane, it is adsorbed on the macromolecular membrane or covalently bound to the macromolecular membrane. The macromolecular membranes include synthetic polymers such as nafion, sodium polystyrene sulfonate, polyvinyl alcohol, polyacrylic acid, polymethacrylic acid, polyacrylamids or natural polymers such as silk, gelation, cellulose and derivatives thereof. These membranes may be used as luminescent probe membranes of the present invention by having the luminescent probe complex adsorbed thereon or embedded therein.

To obtain a polymer in which the luminescent probe complex is introduced by covalent bonding a polymer having polypyridine group constituent is reacted with a bis (polypyridine) type metal complex to produce a tris (polypyridine) type metal complex. The polymer having the polypyridine group constituent can be obtained, for example, by homopolymerizing 4-methyl-4'-vinyl-2,2'-bipyridine or copolymerizing 4-methyl-4'-vinyl-2,2'-bipyridine with another vinyl polymer, or by reacting 4,4'-decarboxy-2,2'-bipyridine with a polymer having amide group. The polymer in which the luminescent probe complex is introduced by covalent bonding may be used as a membrane or may be mixed with another polymer to make a membrane and then used.

The luminescent probe complex is excited by light. The excitation may be performed by irradiating with the light having a wavelength of $\lambda$ max or near $\lambda$ max. The luminescent probe complexes of the present invention are characterized in that a visible light ray may be used as the exciting ray since the complexes have $\lambda$ max in the visible range of 400-500 nm. Any kinds of light sources may be used such as incandescent lamps, xenon lamp, halogen lamp, projector lamps, mercury lamp. The maximum wavelength (E max.) of luminescence is in the vicinity of 600 nm and th eluminescence intensity may be easily measured.

Since the exciting wavelength is separated from the luminescence wavelength by 100-150 nm, luminescence is effectively measured only when light scattering of the exciting light is avoided by using monochromatic light for excitation and by using a cut-off filter to monitor the luminescence.

Further, in case of pH measurement using luminescent probe membrane, a pH measuring device may be obtained by immobilizing the luminescent membrane on the tip of an optical fiber by a known coating method etc. Using this device, it is possible to measure a pH of microenvironments such as living tissues and within cells by monitoring the luminescence through the optical fiber.

BRIEF DESCRIPTION OF THE DRAWINGS

FIGS. 2a and 2b illustrate the relationship between pH values and luminescence intensity of the luminescent probe membrane of the present invention.

BEST MODE FOR CARRYING OUT THE INVENTION

The following examples of the present invention are by way of illustration only and are not intended to be limiting.

EXAMPLE 1

The pH of 2.44 $\mu$M aqueous Ru(DCbpy)$_3^{2-}$ solution was adjusted in the range of pH 3-10 using a buffer solution (phosphoric acid, acetic acid, boric acid). KCl was then added so that the concentration of KCl was 0.5M, and ionic strength was controlled so that it was in the range of 0.50-0.78. The solution thus prepared was introduced in a transparent quartz cell (inner dimensions 1 cm $\times$ 1 cm, height 4 cm) and excited by the light of 468 nm. The luminescence intensity at 640 nm was measured by an emission spectrophotometer. The relationship between the pH and luminescence intensity is shown in FIG. 1.

Figure 1:
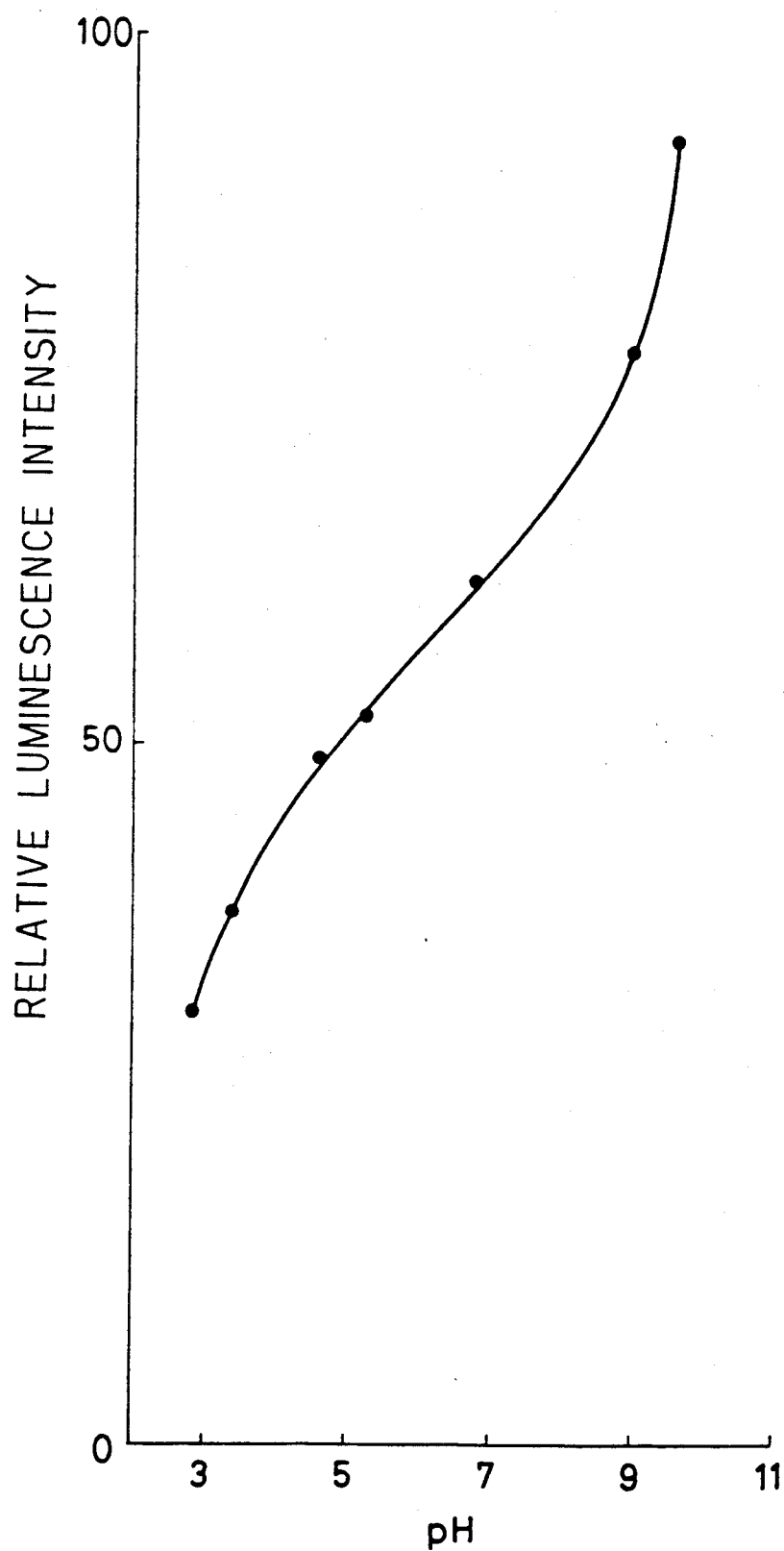
FIG. 1 illustrates the relationship between pH values and luminescence intensity using the luminescent probe complex of the present invention.

By measuring the luminescence intensity of the luminescent probe complex under the same conditions as above the pH of a system can be measured in the range of pH 3-10 by using the relationship of FIG. 1.

EXAMPLE 2

An anion exchange membrane (about 200 $\mu$m in thickness) was immersed in 10 mM aqueous Ru(DCbpy)$_3^{2+}$ solution for four hours, the complex as used in Example 1 was adsorbed on the membrance and dried to produce a luminescent probe membrane according to the present invention. The membrane so obtained was immersed in an aqueous solution having the predetermined pH. Then the relationship between pH and luminescence intensities of the membrane was examined as in Example 1. The results are illustrated in FIG. 2 which shows that the membrane can be used as a luminescent probe membrance for measuring pH.

EXAMPLE 3

4-Vinyl-4'-methyl-2,2'-bipyridine was copolymerized with N-vinyl-pyrrolidone in a molar ration of 1/20 to produce a copolymer having a molecular weight of 10,000. The copolymer and cis-Ru(DCbpy)$_2$Cl$_2$ were reacted under reflux (118° C.) in a medium of xylene/n-butanol = $\frac{1}{4}$ (V$_0$/V$_0$) for 10 hours to synthesize a luminescent probe polymer having the following structure.

Figure 3:
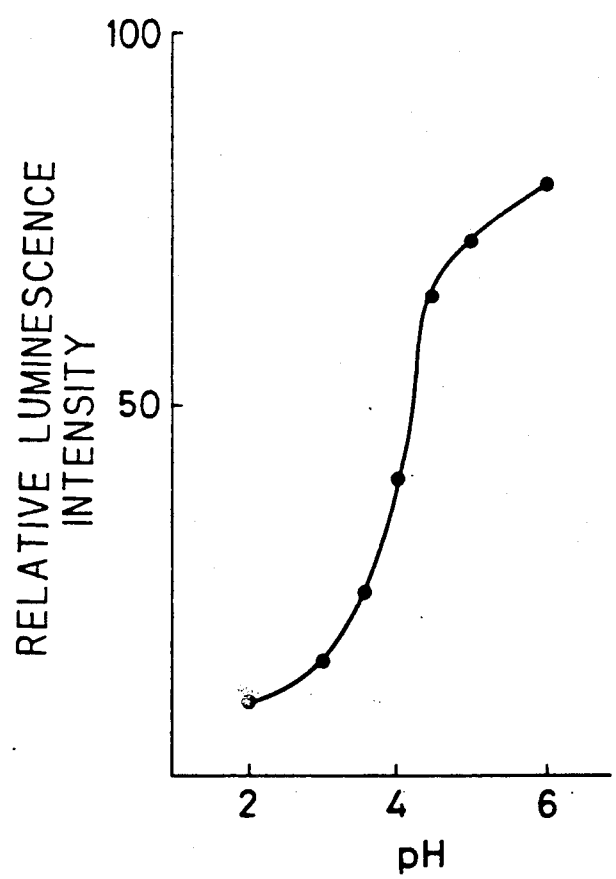
FIG. 3 illustrates the relationship between pH values and luminescence intensity of the luminescent probe polymeric complex of the present invention.

The aqueous solution of the polymer complex was irradiated with monochromic light of 460 nm, and the luminescence intensity at 610 nm was measured. The relationship between the pH and the luminescence intensity was obtained as shown in FIG. 3. The pH of a system in the range of pH 2-6 may be found by measuring the luminescence intensity under the same luminescent probe polymer conditions using the above relationship.

EXAMPLE 4

The luminescent probe polymer as in Example 3 was mixed with gelatin in a weight ratio of $\frac{1}{8}$ (luminescent probe polymer/gelatin) and heated to produce an aqueous solution, which was then cast on a quartz plate and dried to obtain a luminescent probe membrance of about 10 $\mu$m in thickness. The membrane was immersed in a solution, the pH of which had been adjusted by HCl to within the range of 2-6. The luminescence intensity of the membrane was measured. A relationship similar to that in FIG. 3 was obtained. It was found that the luminescent membrane probe may be used to measure a pH in the range of pH 2-6.

EXAMPLE 5

The procedures were repeated in the same manner as in Example 4, except that silk fibroin was used in place of gelatin and an aqueous solution of the luminescent probe polymer and the silk was cast at room temperature. Results similar to that in FIG. 3 were obtained.

EXAMPLE 6

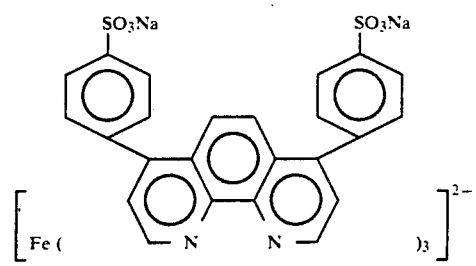

The luminescence intensity obtained by an aqueous tris (vasophenanthroline sulfonic acid) Fe (II) complex solution increases linearly in the range of pH of about 1.5-7. The above aqueous solution could be used in the pH range as a luminescent probe complex according to the present invention.

EXAMPLE 7

The polymer luminescent probe membrane as used in Example 2 was coated on the tip of an optical fiber to obtain a pH sensor. The pH sensor was irradiated with light of 468 nm from a xenon lump. The luminescence was measured with filtering light of below about 500 nm to find the pH.

As explained in detail above, luminescent probe complex, a luminescent probe membrane, a device for measuring pH and a method for measuring pH can be used so as to measure the pH in micro portions easily, which has been considered to be difficult.

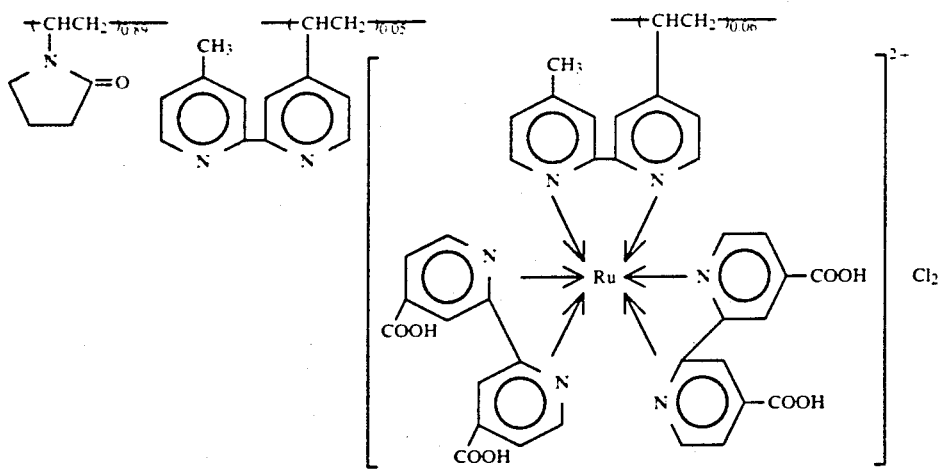

What is claimed is:

1. A device for measuring pH in which pH is measured by determining luminescence intensity of the excited state of a luminescent probe complex in a test solution comprising:

a luminescent probe complex comprising polypyridine ligand having an ion dissociable substituent on a carbon ring and a transition metal ion selected from the elements of group VIII of the periodic table; and a macromolecular membrane which contains said luminescent probe complex and is immobilized at the tip of an optical fiber.

2. A method for measuring pH by determining luminescence intensity of the excited state of luminescent probe complex in a test solution, wherein said device of claim 1 is irradiated with light having a wavelength of λ max or near λ max, and luminescence intensity of the excited state of said luminescent probe complex is measured.

* * * * *